United States Patent [19]

Kutta et al.

[11] Patent Number: 4,791,804

[45] Date of Patent: Dec. 20, 1988

[54] METHOD OF TESTING A COLD GAS FOR THE PRESENCE OF A HAZARDOUS GAS

[75] Inventors: Helmuth W. Kutta, Richardson; Orville C. Morrison, Duncanville, both of Tex.

[73] Assignee: Atlantic Richfield Company, Los Angeles, Calif.

[21] Appl. No.: 107,195

[22] Filed: Oct. 13, 1987

[51] Int. Cl.[4] .............................................. G01N 33/00
[52] U.S. Cl. .......................................... 73/23; 422/83
[58] Field of Search ............... 73/23; 422/83; 340/632

[56] References Cited

U.S. PATENT DOCUMENTS 4,205,043 5/1980 Esch et al. ............................... 73/23

Primary Examiner—John Chapman
Assistant Examiner—Hezron E. Williams
Attorney, Agent, or Firm—F. Lindsey Scott

[57] ABSTRACT

A method and apparatus for testing cold gases for a hazardous gas by flowing the cold gas through a tubing positioined in a garment and then flowing the heated gas from the tubing into a suitable test apparatus.

18 Claims, 1 Drawing Sheet

METHOD OF TESTING A COLD GAS FOR THE PRESENCE OF A HAZARDOUS GAS

BACKGROUND OF THE INVENTION

1. Field of the Invention

This invention relates to a method and apparatus for testing a cold gas at temperature below about −10° F. for the presence of a hazardous gas.

2. Brief Description of Prior Art

In colder climates, difficulty is frequently encountered in testing gaseous mixtures for the presence of hazardous gases. Such hazardous gases may comprise hydrogen sulfide, carbon monoxide, chlorine, light hydrocarbon gases which can constitute an explosive mixture with air, nitrogen oxides, sulfur oxides, carbon dioxide, mercaptans, other heteroatom-containing gases, mixtures thereof and the like. Portable test equipment has been developed and is widely used for testing gases, such as air, to determine whether hazardous gases are present in warmer climates. Unfortunately, such test apparatus has been found to be ineffective and unreliable in colder climates, particularly in very cold climates where temperatures of −20° to −50° F. and colder are encountered. It is desirable to be able to test gases for the presence of hazardous gases at such temperatures prior to the entry of workers and the like into the environment. Since the portable test apparatus used in warmer climates is ineffective at the colder temperatures, it has been necessary to develop other more complicated means for performing these tests. As a result, it has been difficult to obtain timely and frequent tests as necessary to ensure the safety of the atmosphere in working environments in colder climates.

Since it is highly desirable that means for promptly and reliably testing such environments for the presence of hazardous gases be available, a continuing effort has been directed to the development of test apparatus by which such tests can be quickly and reliably performed.

SUMMARY OF THE INVENTION

According to the present invention, a method and apparatus for testing cold gases for a hazardous gas by flowing the cold gas through a tubing positioned in a garment to heat the gas by the body heat of a wearer of the garment and then flowing the heated gas from the tubing into a suitable test apparatus.

Apparatus useful in the conduct of the method of the present invention comprises a garment means including a tubing means positioned in the garment to heat a stream of gas passed through the tubing with the body heat of the wearer of the garment and a test apparatus in fluid communication with the tubing for testing the heated gas for a hazardous gas.

DESCRIPTION OF THE PREFERRED EMBODIMENTS

In the description of the Figures, the same numbers will be used to refer to the same features throughout.

Figure 1:
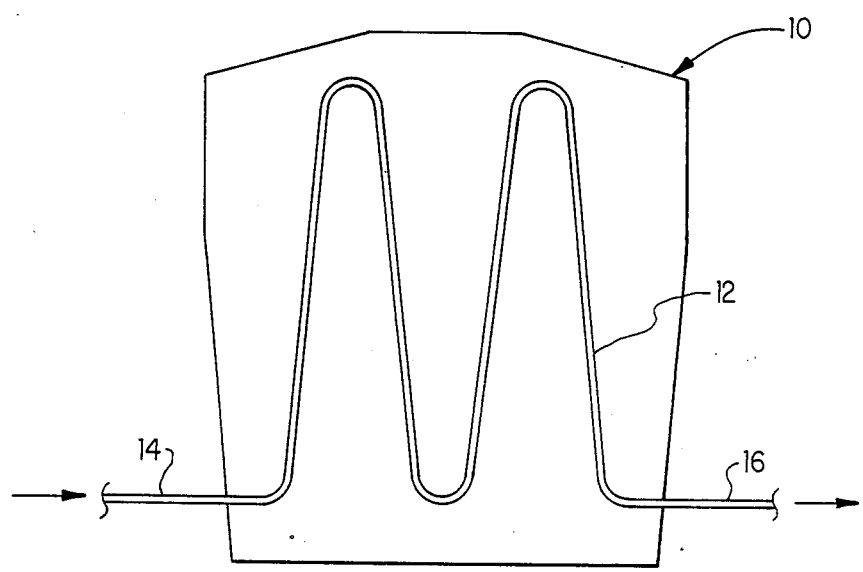
FIG. 1 is a schematic diagram of a back view of a vest garment including a tubing according to the present invention.

In FIG. 1, a rear view of a vest is shown. Vest 10 includes a tubing 12 which includes a tubing inlet 14 and a tubing outlet 16. Tubing 12 may be fabricated from any suitable resilient material such as rubbers, plastics, stainless steel or other suitable metals and the like which are not reactive with the gas tested or the hazardous gas for which the tests are being made. Desirably, tubing 12 is of a suitable wall thickness so that tubing 12 does not kink, crush or otherwise deform to inhibit the flow of gases through tubing 12, but tubing 12 should not be so thick walled or stiff that it is uncomfortable for the wearer of the garment. It is also desirable that tubing 12 be reasonably flexible so that the garment can conform closely to the body of the wearer. Desirably, tubing 12 is positioned near the inner surfaces of the garment so that it is in close contact with the body of the wearer so that body heat can readily be passed to the gas flowing through tubing 12. Desirably, the outer portions of the garment are of a heavy material so that in extremely cold temperatures, the outer portions of the garment insulate tubing 12 against the cold so that tubing 12 is at or near the body temperature of the wearer of the garment. In one embodiment of the present invention the gas to be tested, if under suitable pressure, may be passed directly into inlet 14 through tubing 12 and out outlet 16 to a suitable test apparatus which can be connected to outlet 16 by any suitable means. The test apparatus in this embodiment is desirably insulated although when the gas has been heated to a desired temperature, the gas can be passed to the inlet of a test apparatus which is at a low temperature for a period of time to warm the sensors in the test apparatus even if little or no external instrument insulation is provided.

The gas flow is directly through the sensing apparatus in the tester therefore the sensing apparatus is maintained at or near the temperature of the gas by the flow of the gas so that the test can be performed effectively at the gas temperature.

Figure 2:
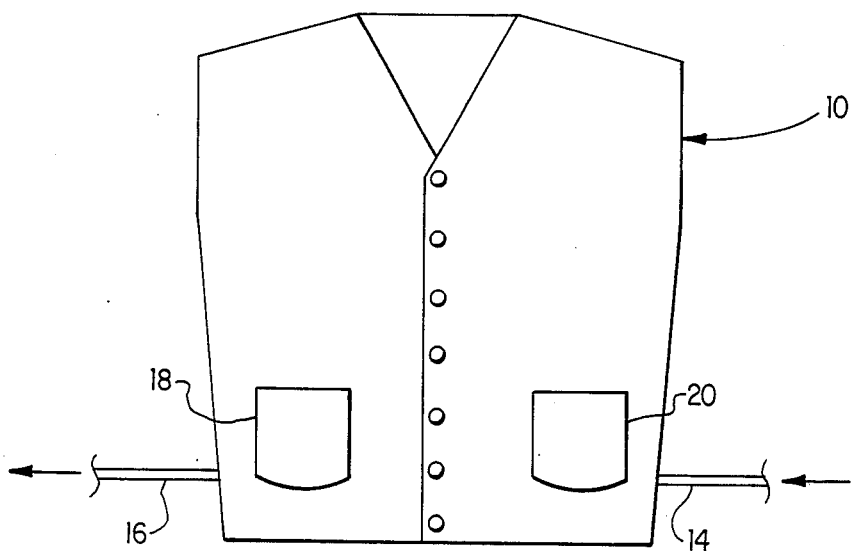
FIG. 2 is a front view of a garment according to the present invention including a battery and a test apparatus.

In an alternate embodiment of the present invention, a pump may be included in garment 10. In FIG. 2, a pocket 18 is shown schematically depicting the inclusion of a pump and desirably batteries in garment 10. A pump (not shown) could be included in a pocket for easy removal and maintenance along with batteries for the pump. The pump and batteries are desirably included in a compartment of garment 10 inside the outer lining of garment 10 so that the pump and batteries can be at a temperature near the body temperature of the wearer. It may be desirable to use rechargeable batteries and to provide means for recharging the batteries during times when the garment is not in use. Rechargeable batteries are well known to the art and if desirable, a plug means can be included in garment 10 so that the batteries can be charged without removing the batteries from garment 10. Similarly, a test apparatus could be included in a compartment 20 shown schematically in FIG. 2 as a pocket in garment 10. The test apparatus could be included in garment 10 in a similar fashion. Even when the test apparatus is included in garment 10 inside the outer lining of garment 10 so that it can be maintained at a higher temperature, tubing 12 is still required since while the instrument is now at a warmer temperature, the sensing elements in the instrument will be effectively functioning at the temperature of the gas to be analyzed. It is therefore still necessary that the gas to be analyzed be heated to a temperature at which the instrument functions effectively. In this embodiment, it may be desirable to include a remote readout from the instrument so that the wearer of the garment can read the test results from a gauge or other display which may be attached to a wire or other suitable means in communication with the test apparatus. Such variations are considered to be known to those skilled in the art.

The hazardous gases most frequently of concern are gases such as hydrogen sulfide, carbon monoxide, chlorine, light hydrocarbon gases which may be present in explosive mixtures with air, nitrogen oxides, sulfur oxides, carbon dioxide, mercaptans, other heteroatom-containing gases, mixtures thereof and the like. While these gases are the most frequently occuring gases, other gases may also be of concern. The apparatus and method of the present invention are considered to be effective in all such applications with the variation that test equipment suitable to the test for the particular hazardous gas or gases in question must be provided. Since test apparatus for determining the presence of hydrogen sulfide, carbon monoxide, chlorine and light hydrocarbons in gaseous mixtures with air are well known to those skilled in the art, no discussion of such test apparatus is considered necessary.

Tubing 12 as discussed previously is desirably suitably resilient to avoid discomfort to the wearer and to avoid deformation of the garment away from the body of the wearer but sufficiently rigid so that kinks and other obstructions to the flow of gas are eliminated. Tubing 12 may desirably be fabricated of rubbers, plastics, stainless steel or other suitable metals and the like. Some particularly suitable materials are polymers of tetrafluoroethylene, and melamine formaldehyde, epoxy, nylon, polycarbonates, polyethylene, phenolformaldehyde, alkyd resins, TYGON and the like.

While the garment shown is a vest, it should be understood that substantially any garment can be used in the practice of the present invention. In general, garments which are easily put on and removed are preferred. Garments which are not part of the wearer's normal attire can be stored in an area near the site at which the test is to be performed until needed then put on by the wearer for the performance of the test. After the test, the garment can be returned to its normal storage space. Some suitable garments include vests, coats, belts, jackets, hats and the like. As indicated previously, other garments could be used, but it is believed that these garments will generally be found most suitable.

Having thus described the invention by reference to certain of its preferred embodiments, it is respectfully noted that many variations and modifications are possible within the scope of the present invention. Such variations and modifications may be considered obvious and desirable by those skilled in the art based upon a review of the foregoing description of preferred embodiments.

Having thus described the invention, we claim:

1. A method for testing a gas at a temperature below about −10 degrees F for the presence of a hazardous gas, said method comprising:
   (a) passing a quantity of said gas through a tubing positioned in a garment and near the inner surface of said garment so that body heat of a wearer of said garment is transferred to said gas flowing through said tubing to heat said quantity of gas with said body heat of said wearer of said garment; and
   (b) analyzing a portion of said heated quantity of gas for the presence of said hazardous gas.

2. The method of claim 1 wherein said gas is at a temperature below −20° F.

3. The method of claim 1 wherein said hazardous gas comprises a gas selected from the group consisting of hydrogen sulfide, chlorine, carbon monoxide, light hydrocarbon gas, nitrogen oxides, sulfur oxides, carbon dioxide, mercaptans, heteroatom-containing gases and mixtures thereof.

4. The method of claim 3 wherein said hazardous gas is hydrogen sulfide.

5. The method of claim 3 wherein said hazardous gas is carbon monoxide.

6. The method of claim 3 wherein said hazardous gas is chlorine.

7. The method of claim 3 wherein said hazardous gas is light hydrocarbon gas.

8. The method of claim 1 wherein said garment is a vest, coat, jacket, belt or hat.

9. The method of claim 1 wherein said tubing is selected from the group consisting of plastics, stainless steel and rubbers.

10. An apparatus for testing a gas at a temperature below about −10 degrees F for the presence of a hazardous gas, said apparatus comprising:
    (a) a garment means including a tubing means positioned in said garment and near the inner surface of said garment so that body heat of a wearer of said garment is transferred to said gas flowing through said tubing to heat a stream of said gas passed through said tubing with said body heat of said wearer of said garment, said tubing including an inlet and an outlet; and
    (b) a test apparatus in fluid communication with said tubing outlet for testing said heated gas for said hazardous gas.

11. The apparatus of claim 10 wherein said tubing is selected from the group consisting of plastics, stainless steel and rubbers.

12. The apparatus of claim 10 wherein said garment includes a pump means for passing said gas through said tubing.

13. The apparatus of claim 10 wherein said garment is a vest, coat, jacket, belt or hat.

14. The apparatus of claim 10 wherein said hazradous gas is hydrogen sulfide and said test apparatus is adapted to test said gas for the presence of hydrogen sulfide.

15. The apparatus of claim 10 wherein said hazardous gas is carbon monoxide and said test apparatus is adapted to test said gas for the presence of carbon monoxide.

16. The apparatus of claim 10 wherein said hazaradous gas is chlorine and said test apparatus is adapted to test said gas for the presence of chlorine.

17. The apparatus of claim 10 wherein said hazardous gas comprises light hydrocarbon gas and said test appartus is adapted to test said gas for the presence of light hydrocarbon gas.

18. The apparatus of claim 10 wherein said garment includes said test apparatus.

* * * * *